(12) United States Patent
Tachibana et al.

(10) Patent No.: US 7,923,897 B2
(45) Date of Patent: Apr. 12, 2011

(54) SONIC FINE-HOLE FORMING APPARATUS

(75) Inventors: Shunro Tachibana, Fukuoka (JP); Katsuro Tachibana, Fukuoka (JP)

(73) Assignee: Sonopore, Ltd., Fukuoka (JP)

(*) Notice: Subject to any disclaimer, the term of this patent is extended or adjusted under 35 U.S.C. 154(b) by 129 days.

(21) Appl. No.: 11/988,188

(22) PCT Filed: Jul. 4, 2005

(86) PCT No.: PCT/JP2005/012357
§ 371 (c)(1),
(2), (4) Date: Feb. 13, 2008

(87) PCT Pub. No.: WO2007/004287
PCT Pub. Date: Jan. 11, 2007

(65) Prior Publication Data
US 2009/0127973 A1    May 21, 2009

(51) Int. Cl.
*H01L 41/00* (2006.01)
*A61N 1/30* (2006.01)
(52) U.S. Cl. .................................. 310/317; 604/20
(58) Field of Classification Search .............. 604/20
See application file for complete search history.

(56) References Cited

U.S. PATENT DOCUMENTS

| | | | |
|---|---|---|---|
| 6,096,000 A * | 8/2000 | Tachibana et al. | 604/20 |
| 6,487,447 B1 | 11/2002 | Weimann et al. | |
| 6,528,039 B2 | 3/2003 | Unger | |
| 6,676,963 B1 | 1/2004 | Lanza et al. | |

FOREIGN PATENT DOCUMENTS

| | | |
|---|---|---|
| JP | 11-009701 | 1/1999 |
| JP | 2004/520852 | 7/2004 |
| WO | WO-01/32232 | 5/2001 |

* cited by examiner

*Primary Examiner* — Nicholas D Lucchesi
*Assistant Examiner* — Jason Flick
(74) *Attorney, Agent, or Firm* — Jordan and Hamburg LLP

(57) ABSTRACT

Disclosed is a sonic fine-hole forming apparatus for forming a fine-hole in a surface of a membrane or solid body in a liquid by means of sonic energy. The sonic fine-hole forming apparatus is adapted to generate a sonic oscillation driving signal comprises a voltage waveform which has positive and negative voltage portions being asymmetrical, and a sharp peak portion. The sonic fine-hole forming apparatus includes a sonic oscillation section having a surface provided with a covering layer or a protective material having an electrically insulating property and a sonic transparency. The coated layer or a protective material is formed to have a thickness of 10 μm or more. The sonic fine-hole forming apparatus of the present invention can form a fine-hole in a surface of a solid body without using a large-scale apparatus, while suppressing a destructive action around the fine-hole.

3 Claims, 5 Drawing Sheets opposite phase range — fundamental wave (a)

(b)

US 7,923,897 B2

SONIC FINE-HOLE FORMING APPARATUS

TECHNICAL FIELD

The present invention relates to a sonic fine-hole forming apparatus for forming a fine-hole in a surface of a membrane or solid body in a liquid by means of sonic energy.

BACKGROUND ART

Heretofore, a laser process, an electroporation process and a microneedle process have been known as a technique for forming a large number of fine-holes having a microscale or nanoscale diameter, in a surface of a membrane or solid body in a liquid.

Sonic energy and ultrasonic energy have been industrially utilized for cleaning and disintegrating/breaking. In the medical fields, ultrasonic energy has also been widely used for diagnoses of cardiac diseases, abdominal diseases and head/neck diseases. For the purpose of medical treatments, a powerful sonic wave (e.g., shock wave) has been used for destructing gallstones or kidney stones, and thermal energy converted from sonic energy has been used for locally burning a site of cancer. Research on application of ultrasonic energy for assisting penetration of a drug into body tissues is being carried out (see the following patent Publications 1 and 2).
[Patent Publication 1] U.S. Pat. No. 6,676,963
[Patent Publication 2] U.S. Pat. No. 6,528,039

DISCLOSURE OF THE INVENTION

Problem to be Solved by the Invention

It is not easy to form a large number (e.g., one to one million/$mm^2$) of fine-holes (e.g., diameter: 1 mm to 10 nm) in a surface of a membrane or solid body in a liquid. Laser is unsuitable for forming a fine-hole because it is undesirably absorbed and scattered in a liquid. The microneedle process and the electroporation process have difficulty in forming a large number of fine-holes with practical stability and efficiency. It is known that a hole-forming technique utilizing the intermediate phenomenon between destructive and non-destructive actions of sonic energy is possible. There are also techniques of forming a fine-hole in a membrane or solid body using a jet flow which is instantaneously generated by sonically bursting fine-bubbles (diameter: 0.1 mm to 0.1 μm) formed using ultrasonic energy. However, it is generally considered extremely difficult to control the generation and destruction of bubbles as desired. The major reason is that a target sound field has significant complicated non-linear characteristics and therefore such a control cannot be achieved using a general-purpose sonic oscillation element and driving power supply adapted to generate only a sonic wave having a single frequency, sound pressure and waveform. Moreover, an adequate sound field cannot be created without using expert knowledge and advanced techniques and satisfying limited conditions. Thus, the above technique can be used only for significantly limited purposes. In some situations, it is often the case that even researchers and engineers who are not specialists in acoustics face the necessity of forming a fine-hole in various scenes. Thus, if a technique capable of forming a fine-hole in a surface of a membrane or solid body in a liquid without using a large-scale apparatus is developed, a phenomenological principle of the technique can be used widely and generally.

If a sonic oscillation section is brought closer to or into contact with an object to be formed with a fine-hole, the object is highly likely to be destroyed before forming a fine-hole therein, due to enhancement in mechanical destructive action of sonic energy. This stands as a major obstacle for achieving a stable sound field and optimal conditions required for forming a fine-hole. Presently, there is not other apparatus capable of forming a fine-hole while suppressing a destructive action in a vicinity of (e.g., within 2 mm around) a vibrated surface of a target object.

In view of the above circumstances, it is an object of the present invention to provide a sonic fine-hole forming apparatus capable of forming a fine-hole in a surface of a solid body without using a large-scale apparatus, while suppressing a destructive action around the fine-hole.

Means for Solving the Problem

A sonic fine-hole forming apparatus of the present invention is generally classified into a sonic oscillation section and a driving power supply section. A fine-hole can be formed accurately and stably only if each of the sonic oscillation section and the driving power supply section are optimally set in certain conditions. A plurality of sonic oscillation sections different in size, number and configuration are prepared, and one of the sonic oscillation sections is selected depending on an intended purpose.

A frequency, amplitude, waveform and pulse-switching of an oscillation driving signal to be generated by a driving power supply unit for supplying electric energy are pre-programmed. Further, information about electrical impedance, temperature, resonance, etc., is fed back from a sensor installed in the sonic oscillation section to a CPU in a main unit of the apparatus, to controllably adjust the oscillation driving signal so as to allow a fine-hole to be more stably formed. An electrical parameter of the oscillation driving signal to be controllably adjusted includes a frequency (1 Hz to 20 MHz), a voltage (0.1 V to 200 V), a waveform, a burst-wave duration, a burst-wave repetition frequency (0.01 Hz to 100 Hz), a phase (zero to 360 degrees), a duty ratio (zero to 100%), and a pulse-wave on/off frequency (0.01 Hz to 100 Hz). It is necessary to ensure an electrical output of 1 mW up to 400 W.

The oscillation driving signal has a waveform which is different from a commonly-used simple waveform, such as a rectangular wave, a sine wave or a sawtooth waveform. Specifically, in order to form a fine-hole more efficiently than ever before, an asymmetrical waveform is used, as shown in FIG. 1(a), wherein a voltage waveform of the signal per cycle essentially has positive and negative voltage portions being asymmetrical, and a sharp peak portion.

An on/off switching of a burst wave and/or a pulse wave to be sonically oscillated can be rigorously controlled to obtain a stable fine-hole forming function. Specifically, when a sonic oscillation operation is temporarily stopped, the oscillation driving signal is typically switched to a zero voltage. In this case, with a view to fully eliminate natural vibration of an oscillation element and echosound in a surrounding sound field just after the cease of the oscillation operation, a voltage having an opposite phase shift, i.e., a phase difference of 180 degrees relative to that of a fundamental wave, may be applied just after termination of the oscillation driving signal, to positively create a silent state. This rigorous silent state may be frequently created to set desirable conditions allowing a fine-hole to be formed efficiently and stably. A similar phenomenon occurs when a sonic wave is generated using an oscillation driving signal having a randomly changed frequency and when the sonic oscillation section is driven using a so-called "white noise" signal, as shown in FIG. 1(b). Specifically, in case of driving the sonic oscillation section by applying an oscillation driving signal having each block of a random frequency in a stepwise manner, sonic energy is generated when the frequency conforms to a resonance frequency of the sonic oscillation section (the resonance frequency varies depending on a size, configuration and material of the sonic oscillation section). Then, in another moment, the sonic oscillation section will be driven by an oscillation driving signal having a frequency completely different from the resonance frequency. Thus, sonic vibration is rapidly erased to create a silent state. This phenomenon should repeatedly occur to allow sonic energy to be effectively utilized. The random frequency signal or the white noise signal is generated according to a random number table in such a manner that a change in frequency thereof falls within ±10% with respect to a center frequency. The rate of the burst change is set in the range of 1 Hz to 300 Hz. The present invention is distinctively characterized by a fundamental technique where the above principle is incorporated in an electrical program circuit of the driving power supply section to efficiently oscillate sonic energy.

As shown in FIG. 2, with a view to protecting a sonic oscillation element 1, a sonic vibration portion 3, such as a PZT (piezoelectric zirconate titanate) vibrator, may be surroundedly covered by with a protective layer 2 made of a material having an electrically insulating property and a high sonic transparency, such as polyethylene, nylon, urethane or silicone. This protective layer 2 makes it possible to efficiently form a fine-hole in a target object while avoiding an unwanted destructive action. The protective layer 2 may be formed to have a thickness of about 10 µm to 1 cm, without taking account of a configuration of the sonic oscillation element 1.

Alternatively, as shown in FIG. 3, a sonic oscillation element 1 connected to a sonic element driving electrode 1a may be surrounded by a fluid material 4e having an electrically insulating property and a high sonic transparency, such as ultrapure water, distilled water, hydrogel, liquid paraffin, oil or fat, in such a manner that the fluid material 4 is enclosed in a thin covering layer 5 made of polyethylene, nylon, urethane, silicone or the like, together with the sonic oscillation element 1, to obtain the same effect. The covering layer 5 may be formed to have a thickness of about 10 µm to 1 cm. In this case, a distance between a vibrating surface of sonic oscillation element 1 and the covering layer 5 is essentially set at a value equal to or greater than a vibrational amplitude of the vibrating surface. Further, it is necessary to adjust a viscosity of the fluid material 4 enclosed in the covering layer 5 so as to prevent air bubbles or the like from being generated in the fluid material 4. When the sonic oscillation element 1 has a planar shape, a central portion thereof has a largest vibrational amplitude. Thus, a vibrating surface of the central portion should be covered by a solid or fluid material having a larger thickness than that for the remaining portion. In FIG. 3, the reference numeral 6 indicates an impedance electrode for measuring a resistance of the fluid material 4, and the reference numeral 7 indicates a temperature sensor.

Effect of the Invention

The sonic fine-hole forming apparatus of the present invention can form a fine-hole in a surface of a solid body without using a large-scale apparatus, while suppressing a destructive action around the fine-hole.

BEST MODE FOR CARRYING OUT THE INVENTION

In the medical fields and the biological research fields, it is often necessary to inject various substances, such as genes, drugs and chemical materials, into cells or tissues. For this purpose, it is necessary to form a fine-hole in a surface of a cell or tissue.

As shown in FIGS. 4(a) and 4(b), in a sonic fine-hole forming apparatus according to one embodiment of the present invention, a sonic oscillation element 1 of a sonic oscillation section is inserted into a cell culturing medium vessel 8 which contains a culture solution including a large number of cultivated cancer cells, through a protective layer 2. Then, a substance to be injected into cancer cells is added to the culture solution, and a driving power supply is activated. In response to the activation of the driving power supply, sonic energy is emitted to the cancer cells to form a large number of fine-holes in a surface of each of the cancer cells. The substance, such as a gene, a drug or a chemical material, flows into the cancer cell through the fine-holes. Most biological cells can exist only in environments close to an aqueous solution. Thus, it is important that the present invention is effectively implementable in a liquid. In the conventional techniques, a cell is likely to be destroyed by sonic energy. By contrast, in this embodiment, the sonic oscillation section including the sonic oscillation element 1 is surrounded by a covering layer including the protective layer 2, so that damages to the cells can be minimized. In addition, the sonic oscillation section 1 is designed to be driven using an electrical oscillation wave signal which comprises a random frequency signal, a white noise signal and an opposite-phase shift waveform signal, and has an asymmetrical voltage waveform with a sharp peak portion, so as to evenly form fine-holes in each of the cells. In another embodiment of the present invention, a sonic vibration portion of the sonic oscillation element 1 may be pre-incorporated into a bottom portion of the cell culturing medium vessel 8. In this case, the operation of inserting the sonic oscillation element 1 into the culture solution can be omitted. Thus, a plurality of cell culturing medium vessels each incorporating the sonic vibration portion can be prepared to simultaneously emit a sonic wave to a larger number of cells. The sonic vibration portion may be reduced in size to efficiently form fine-holes in the cells even if only a fairly small amount of culture solution is contained in the cell culturing medium vessel 8. In order to simultaneously drive a plurality of sonic oscillation elements 1, a plurality of feed lines for the respective elements 1 may be connected in parallel to a sonic element driving electrode 1a.

In a drive unit illustrated in FIG. 5, the reference numeral 11 indicates a frequency indicator; 12 indicates a pulse frequency and duty ratio indicator; 13 indicates an output indicator; 14 indicates a timer time indicator; 15 indicates a temperature indicator; 16 indicates a frequency adjust knob; 17 indicates a pulse adjust knob; 18 indicates a duty ratio adjust knob; 19 indicates an output adjust knob; 20 indicates a timer adjust knob; and 21 indicates a white-noise/random-frequency switching knob. A temperature, voltage, electrical energy (W) consumption, driving frequency (frequency counter), duty ratio (%) and burst frequency (Hz) are actually measured in the sonic oscillation section, and these data are indicated at the drive unit. The drive unit is adapted to automatically turn on/off the driving power supply according to an automatic timer (0.1 to 3600 sec). The drive unit is also provided with a selector switch for optimizing the driving signal based on the data fed back from the sonic oscillation section, and a selector switch for selecting one of a plurality of sonic-energy effective utilization modes each using a different sonic oscillation driving signal, such as a random frequency signal, a white noise signal and an opposite-phase shift waveform signal.

In addition to a cell in a culture solution, the sonic fine-hole forming apparatus can form a fine-hole in a surface of a cell in a living body by emitting a sonic wave to the cell using the sonic oscillation section. For example, several sonic oscillation sections are aligned in a line, and inserted into a digestive tract or a blood vessel so as to form a large number of fine-holes in a surface of a cell or biological tissue therearound. Through the large number of fine-holes, a drug for a central nervous system, a peripheral nervous system, a sense organ, a circulatory organ, a respiratory organ or a digestive organ, a hormone drug, a genitourinary drug, a dermatological drug, a thrombolytic agent, an anticancer drug, an antiallergic drug, an antibiotic drug, a metabolic agent, a gene therapeutic agent, a diagnostic contrast medium, a stain, a light-sensitive drug, an ultrasonic drug, a vasodilative agent, a new blood vessel depressant, a vitamin, an antioxidant agent, an antiinflammatory agent, etc, can be efficiently administered. The sonic fine-hole forming apparatus may also be used in an experimental test on cloning of animal egg, chicken embryo, mouse embryo stem cells, ES cells or bovine embryo. Furthermore, for the purpose of improvement in plant varieties, the sonic fine-hole forming apparatus may be used in forming a fine-hole in a cell wall of a plant. In industrial applications, the sonic fine-hole forming apparatus may be used for forming a large number of fine-holes in a surface of a membrane or material incapable of being dried.

In another embodiment of the present invention, during use of the sonic fine-hole forming apparatus, a microscale or nanoscale particle made of lipid or polymer a microscale or nanoscale capsule encapsulating gas may be used in combination to more efficiently form a fine-hole. As a typical example, nanoparticles (nanosized particles) of an existing ultrasonic contrast medium or MRI contrast medium or a diagnostic/therapeutic drug having a property of accumulating in a specific tissue may be mixed in a liquid and used in combination with the sonic fine-hole forming apparatus, to more stably form a large number of fine-holes. The sonic fine-hole forming apparatus is adapted to adjust a size of a fine-hole and the number of fine-holes per area.

Example 1

An aluminum foil of 1 cm×1 cm was immersed in water, and a sonic wave was generated from the sonic oscillation section of the present invention set in the following conditions: random frequency=around 2 MHz (+0.1 MHz); pulse frequency=30 Hz; and sonic-wave irradiation time=60 sec, and emitted onto a surface of the aluminum foil. As a result, ten thousand fine-holes having a size of about 10 μm could be formed in 1 mm×1 mm area on an average.

Example 2

The sonic oscillation section of the present invention was used in introducing a gene into a chicken limb bud (stages 20 to 21). A chicken egg was grown in an incubator held at a temperature of 38.5° C. and a given humidity until an intended stage. A hole was opened in a blunt end of an egg shell, and 4 to 5 ml of egg content was taken out through the hole using a syringe having an 18 G needle attached thereto. An upper portion of a lateral surface of the egg shell was cut out using an ophthalmic knife to form a round window therein. A gene [GFP (pEGFP), LacP (pEF-LacZ)] was directly injected into a limb bud through the window under microscopic observation. Then, the sonic oscillation section of the present invention was inserted into the egg through the window until it reaches a vicinity of a target region. An operation of forming fine-holes in the target region to introduce the gene thereinto was performed under the following conditions: ultrasonic energy=2.0 W/cm$^2$; duty cycle=20%; sonic-wave irradiation time=60 sec; sonic oscillation driving signal=random frequency signal. As a result, an expression vector could be introduced into the limb bud to obtain an expression level 50 times of that in a conventional electroporation process. The expression of a GFP gene is transient. Thus, a GFP gene expression already started after 3 hours from the introduction, and reached a peak after an elapse of 12 hours. Then, almost no GFP gene expression was observed before an elapse of 48 hours. A LacZ gene expression was observed in the limb bud even after 12 hours from the gene introduction. In case of using an expression vector (pCAGGS-cShh) for a Shh gene in the same manner, it was verified that supernumerary toes can be induced.

Example 3

A cavity was formed in a flesh extracted bovine front tooth to extend from a root up to a pulp thereof using a turbine diamond round bar #440, a plasmid (TIMP-pEGFP) having a TIMP promoter associated with pEGFP-N3 (Clontech, Palo Alto, Calif.) was injected into the cavity. An ultrasonic contrast medium (Optison: Molecular Biosystems Inc, San Diego, Calif.) was pre-mixed with the plasmid DNA (25 μg) at a ratio of 1:3. An internal space of the cavity was filled with a liquid (Ultra/Phonic Conductivity Gel: Nishimoto Sangyo Co., Ltd.), and a sonic wave was emitted from above a surface of the Gel using the sonic fine-hole forming apparatus of the present invention. The ultrasonic wave was set to have an intensity of 0.5 W/cm$^2$ or 1 W/cm$^2$ and a frequency of 1 MHz (sonic-wave irradiation time=15, 30 and 60 sec). Then, the tooth pulp was extracted, and subjected to a Trowell-type organ culture in a 10% bovine serum-containing DMEM. After 24 hours, a fluorescence of GFP (green fluorescent protein) was checked through observation using a stereoscopic fluorescence microscope.

As a result, the GFP fluorescence was significantly observed in the tooth pulp irradiated with the ultrasonic wave. This proves that a large number of fine-holes were formed in tissues and a surface layer of the tooth pulp. In this manner, it was verified that gene introduction efficiency is effectively enhanced, and is dependent on the ultrasonic-wave intensity and the ultrasonic-wave irradiation time. In case of setting a frequency of the sonic fine-hole forming apparatus at 1 MHz, it was considered that, under the following conditions: ultrasonic-wave intensity=0.5 W/cm$^2$; sonic oscillation driving signal=white noise signal; and ultrasonic-wave irradiation time=30 sec, the GFP is most diffusely distributed over the pulp tissues in the cavity, without significant damages in the pulp tissues, and the gene introduction efficiency is optimized.

Example 4

An influence on vascular endothelial tissues was experimentally checked. 20 μg of TIMP-pEGFP plasmid was applied to a vascular endothelial tissue, and an ultrasonic wave was emitted from the sonic oscillation section of the present invention set in the following conditions: intensity=0.5 W/cm$^2$; frequency=1 MHz; and irradiation time=30 sec. After an organ culture for one day, the tissue was rapidly frozen. A piece of the frozen tissue having a size of 20 μm was prepared, and a fluorescence of GFP in the tissue was checked through observation of a computer image using a confocal laser scanning microscope (LSM 410, argon laser, B 488 nm, 30 mW: Carl Zeiss AG). Additionally, the presence of inflammation and necrosis was checked through HE (hematoxylin/eosin) staining.

The vascular endothelial tissue subjected to the organ culture for one day after the gene introduction was HE-stained and observed. As a result, neither inflammation nor necrosis was observed. Then, a computer image of the GFP fluorescence was analyzed under observation using the confocal laser scanning microscope. As a result, it was proven that the introduced GFP gene is incorporated into the tissue up to a depth of 200 μm from a surface thereof.

Example 5

The sonic oscillation section of the sonic fine-hole forming apparatus of the present invention was inserted into an artificial blood vessel formed in a blood vessel of an abdominal aorta of a river eel. Then, a sonic wave was emitted to the artificial blood vessel under the following conditions: intensity=1 W/cm$^2$; frequency=2 MHz; and irradiation time=30 sec, and a thrombolytic agent was added into the artificial blood vessel. As a result, as compared with comparative samples irradiated with no sonic wave, thrombolysis was observed in the artificial blood vessel in a significantly shorter period of time. This would result from a larger number of fine-holes formed in a surface of a blood clot.

EXPLANATION OF CODES

Figure 1:
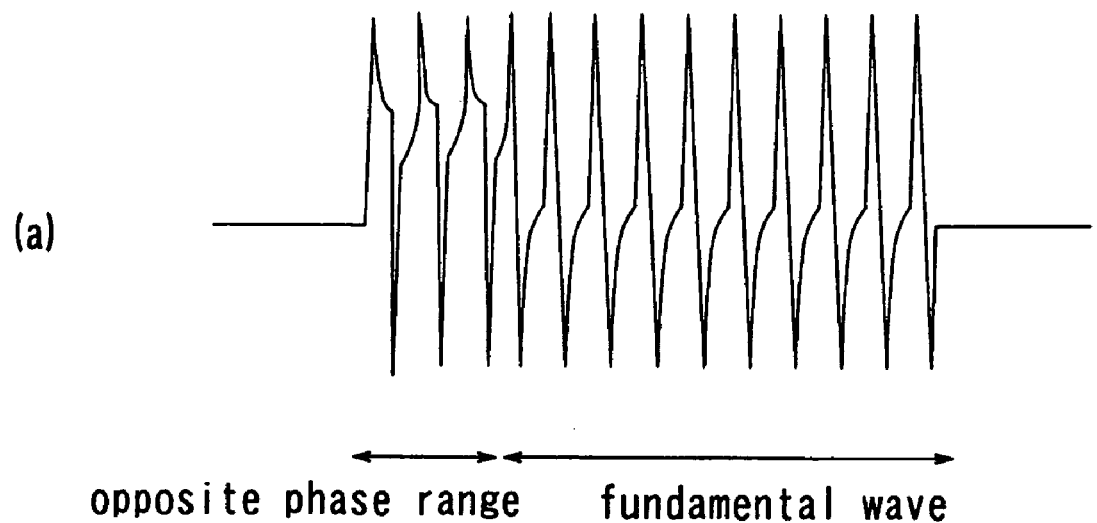
FIGS. 1(a) and 1(b) are charts showing a waveform for use in a sonic fine-hole forming apparatus according to one embodiment of the present invention.
Figure 1:
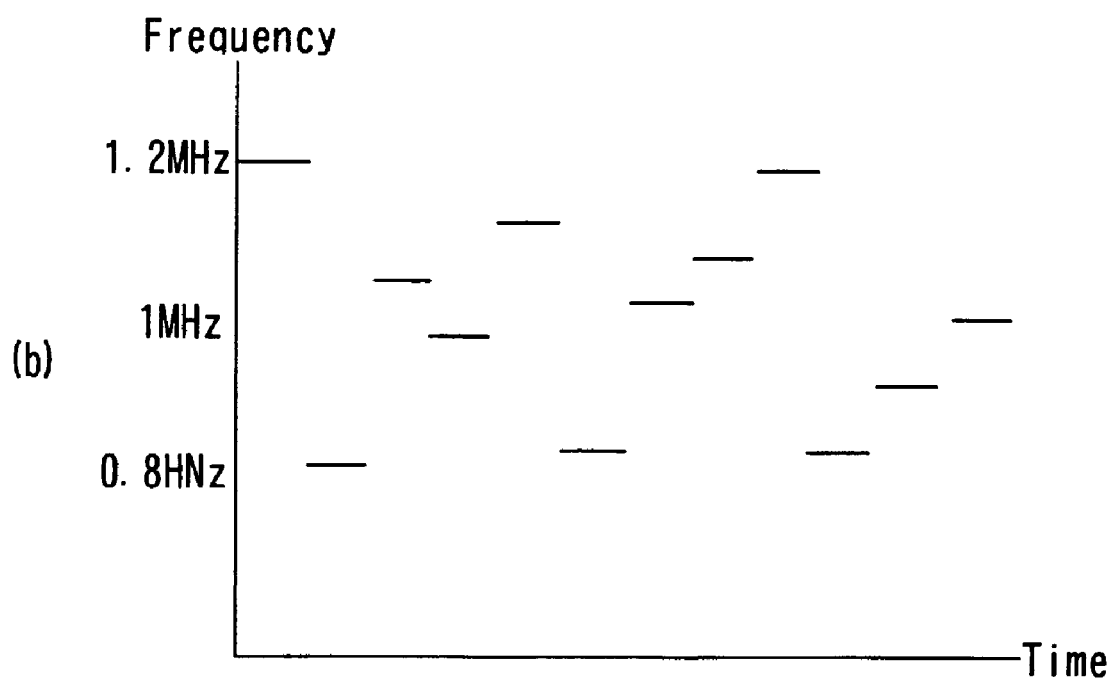
Figure 2:
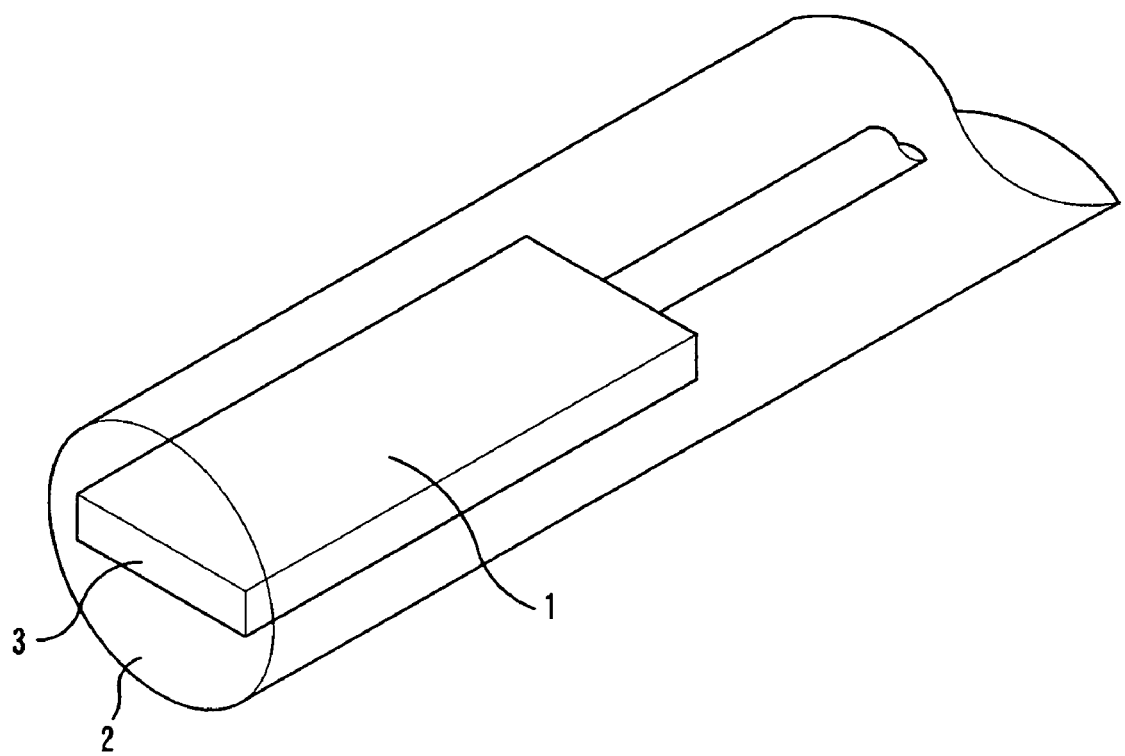
FIG. 2 is a schematic diagram showing one example of a sonic oscillation section of the sonic fine-hole forming apparatus according to the embodiment.
Figure 3:
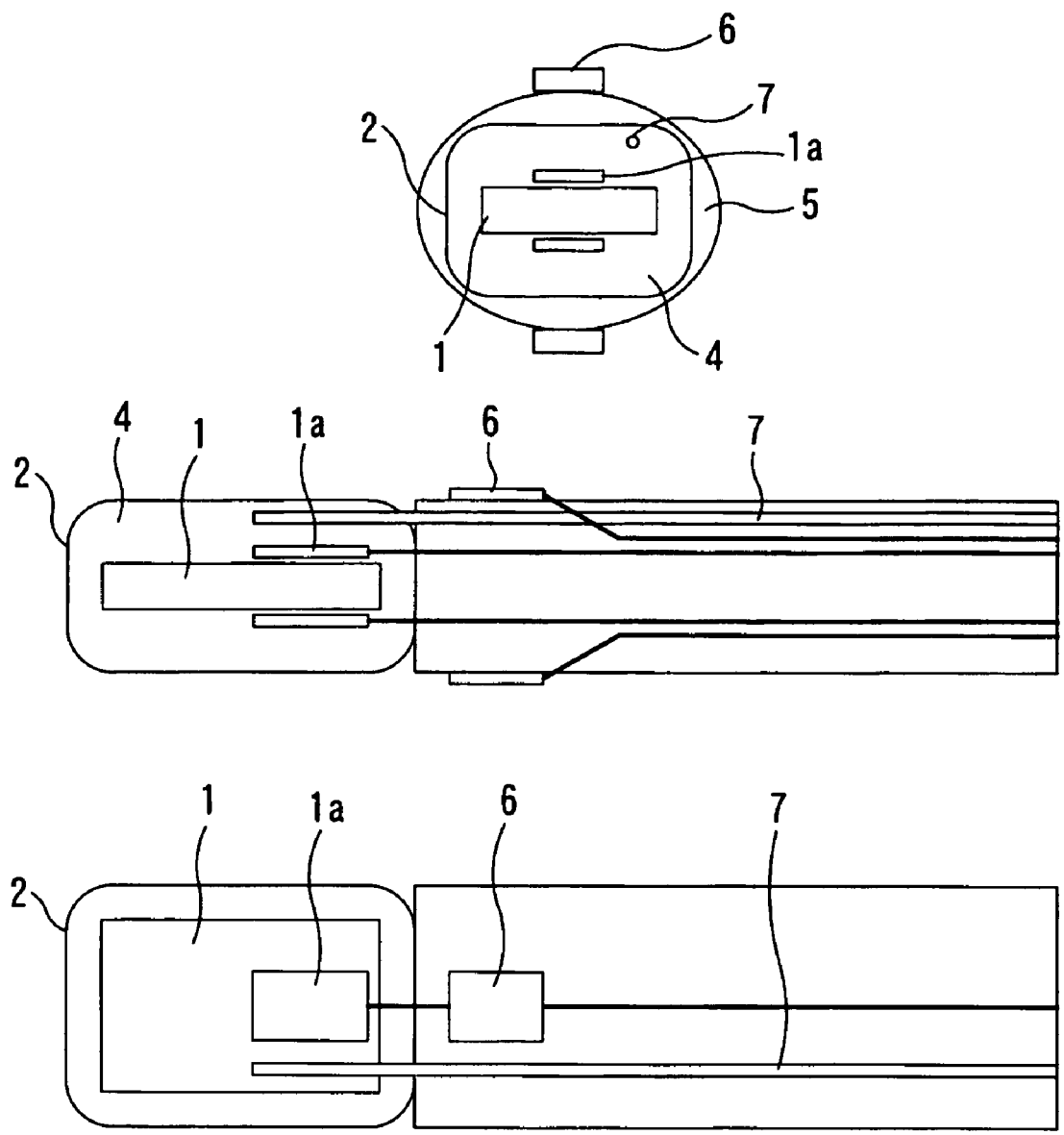
FIG. 3 is a schematic diagram showing another example of the sonic oscillation section.
Figure 4:
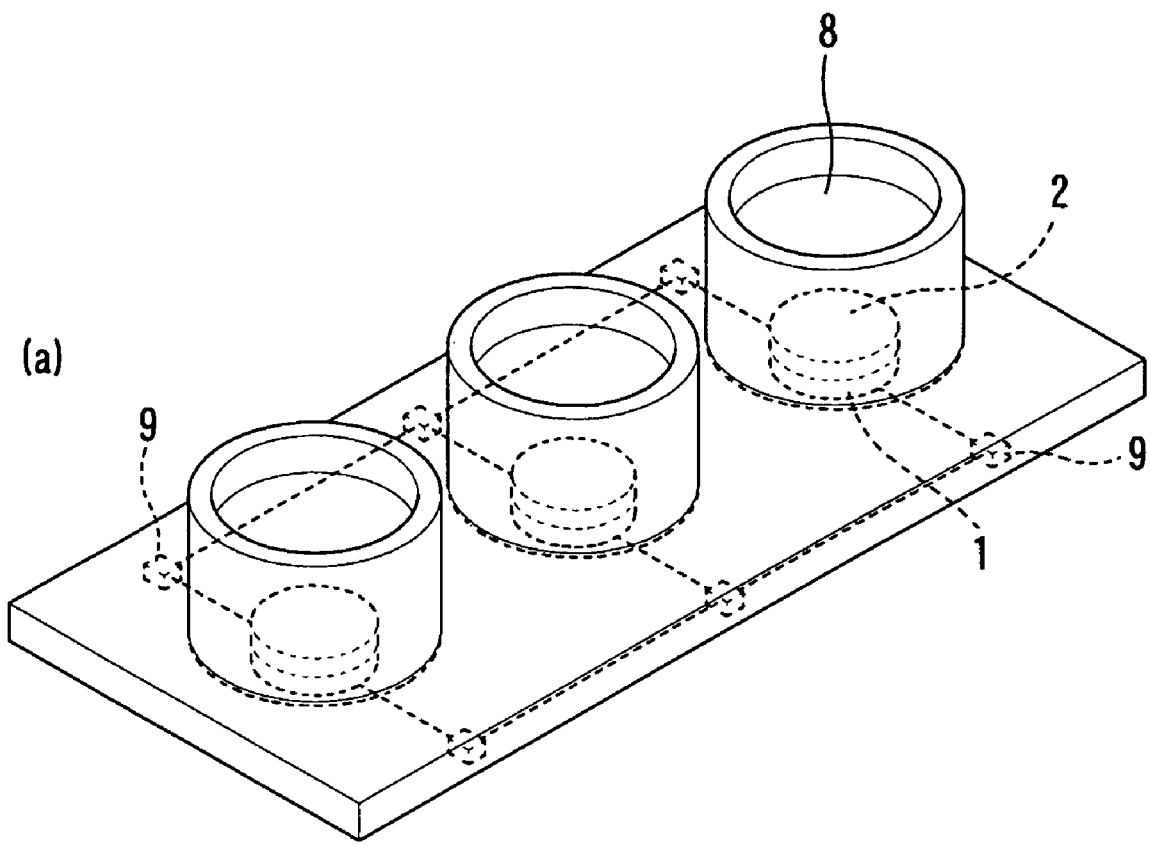
FIGS. 4(a) and 4(b) are schematic diagrams showing a sonic fine-hole forming apparatus according to another embodiment of the present invention.
Figure 4:
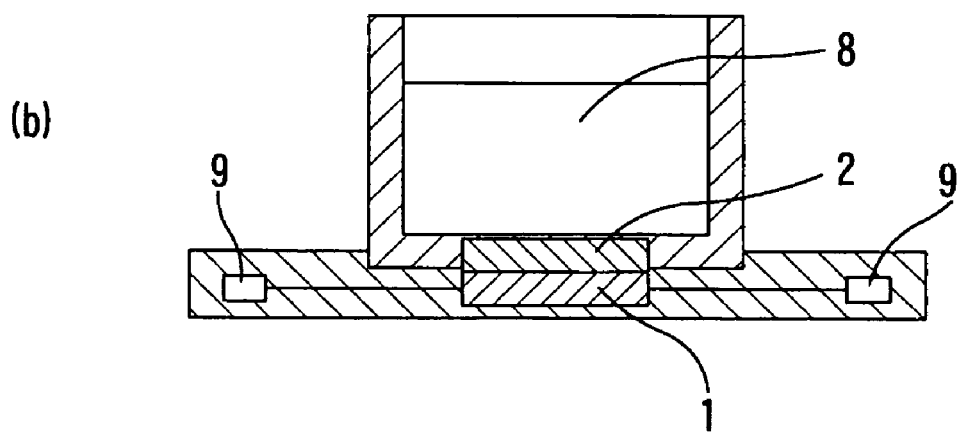
Figure 5:
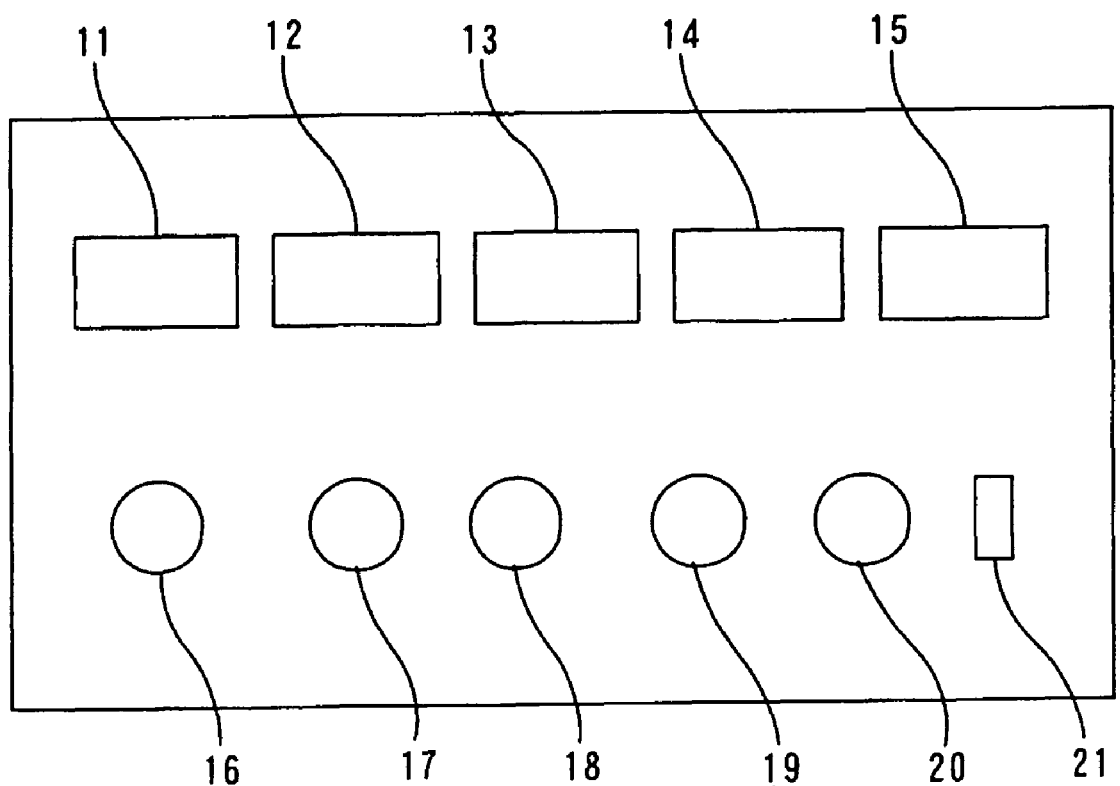
FIG. 5 is a schematic diagram showing one example of a drive unit of a sonic fine-hole forming apparatus of the present invention.

1: sonic oscillation element
1a: sonic element driving electrode
2: protective layer
3: vibration portion
4: fluid material
5: covering layer
6: impedance electrode
7: temperature sensor
8: cell culturing medium vessel
9: network matching circuit
11: frequency indicator
12: pulse frequency and duty ratio indicator
13: output indicator
14: timer time indicator
15: temperature indicator
16: frequency adjust knob
17: pulse adjust knob
18: duty ratio adjust knob
19: output adjust knob
20: timer adjust knob
21: white-noise/random-frequency switching knob

What is claimed is:

1. A sonic fine-hole apparatus for forming a fine-hole in a surface of a membrane or solid body in a liquid by means of sonic energy, said sonic fine-hole forming apparatus comprising a sonic oscillation driving signal generator configured to generate a voltage waveform which has positive and negative voltage portions that are asymmetrical, and the positive and negative portions each having a sharp peak portion, a sonic oscillation section defining an interior cavity housing a sonic oscillation element and a fluid surrounding said sonic oscillation element, said sonic oscillation element being a sonic transducer configured to deliver sonic energy and driven by said oscillation driving signal generator, said sonic oscillation section having a surface formed by a covering layer defining said interior cavity and said covering layer having an electrically insulating property and a sonic transparency, said covering layer being formed to have a thickness of 10 μm or more and to be continuous without openings so as to seal the interior cavity of the sonic oscillation section from an environment exterior to said covering layer and contain the membrane or solid body.

2. A sonic fine-hole forming apparatus for forming a fine-hole in a surface of a membrane or solid body in a liquid by means of sonic energy, said sonic fine-hole forming apparatus comprising:
a sonic oscillation section including a sonic transducer;
a signal generator connected to drive said transducer with a drive signal, said signal generator being configured to produce said drive signal as a waveform which has pointed sharp positive peaks and pointed sharp negative peaks which are asymmetric about a zero axis by virtue of concaved waveform portions being on a first side of the zero axis and not on a second side of the zero axis in a given period of the waveform, and the waveform having linear portions interconnecting said pointed sharp positive peaks with said pointed sharp negative peaks, said sonic oscillation section defining an interior cavity housing a sonic oscillation element and a fluid surrounding said sonic oscillation element, said sonic oscillation element being a sonic transducer configured to deliver sonic energy and driven by said oscillation driving signal generator, said sonic oscillation section having a surface formed by a covering layer defining aid interior cavity and having an electrically insulating property and a sonic transparency, said covering layer being formed to have a thickness of 10 μm or more and to be continuous without openings so as to seal the interior cavity of the sonic oscillation section from an environment exterior to said covering layer and contain the membrane or solid body.

3. A sonic fine-hole forming apparatus for forming a fine-hole in a surface of a membrane or solid body in a liquid by means of sonic energy, said sonic fine-hole forming apparatus comprising: a sonic oscillation section including a sonic transducer and having a resonant frequency; a signal generator connected to drive said transducer with a drive signal, said signal generator being configured to produce said drive signal including a first portion at said resonant frequency which is followed by a second portion at a second frequency different from said resonant frequency and so as to produce a silent state by application of the second frequency, said sonic oscillation section defining an interior cavity housing a sonic oscillation element and a fluid surrounding said sonic oscillation element, said sonic oscillation element being a sonic transducer configured to deliver sonic energy and driven by said oscillation driving signal generator, said sonic oscillation section having a surface formed by a covering layer defining said interior cavity and having an electrically insulating property and a sonic transparency, said covering layer being formed to have a thickness of 10 μm or more and to be continuous without openings so as to seal the interior cavity of the sonic oscillation section from an environment exterior to said covering layer and contain the membrane or solid body.

* * * * *